(12) United States Patent
McMillan et al.

(10) Patent No.: US 9,517,023 B2
(45) Date of Patent: Dec. 13, 2016

(54) METHOD AND SYSTEM FOR DIRECTING A LOCALIZED BIOLOGICAL RESPONSE TO AN IMPLANT

(75) Inventors: William A. McMillan, Cupertino, CA (US); Natalie Wisniewski, San Francisco, CA (US)

(73) Assignee: Profusa, Inc., South San Francisco, CA (US)

( * ) Notice: Subject to any disclaimer, the term of this patent is extended or adjusted under 35 U.S.C. 154(b) by 621 days.

(21) Appl. No.: 12/789,048

(22) Filed: May 27, 2010

(65) Prior Publication Data

US 2010/0303772 A1 Dec. 2, 2010

Related U.S. Application Data

(60) Provisional application No. 61/182,995, filed on Jun. 1, 2009.

(51) Int. Cl.
*A61B 5/145* (2006.01)
*A61K 9/70* (2006.01)
*A61K 9/00* (2006.01)

(52) U.S. Cl.
CPC ....... *A61B 5/14503* (2013.01); *A61B 5/14532* (2013.01); *A61K 9/0024* (2013.01); *A61K 9/7038* (2013.01)

(58) Field of Classification Search
None
See application file for complete search history.

(56) References Cited

U.S. PATENT DOCUMENTS

| | | | |
|---|---|---|---|
| 4,703,756 | A | 11/1987 | Gough et al. |
| 5,284,140 | A | 2/1994 | Allen et al. |
| 5,777,060 | A | 7/1998 | Van Antwerp |
| 5,895,658 | A | 4/1999 | Fossel |

(Continued)

FOREIGN PATENT DOCUMENTS

| | | |
|---|---|---|
| JP | 2004-537344 A | 12/2004 |
| JP | 2008/541881 | 11/2008 |

(Continued)

OTHER PUBLICATIONS

Cordiero, P.G., et al. The protective effect of L-arginine on ischemia-reperfusion injury in rat skin flaps. Plast Reconstruct Surg. 1997. 100(5):1227-1233.

(Continued)

*Primary Examiner* — Robert T Crow (57) ABSTRACT

The invention provides methods for directing a localized biological response of a mammalian body to an implant disposed within the body. In one embodiment, a delivery system is positioned outside the body and adjacent to the implant within the body. The delivery system comprises a first tissue response modifier effective for directing a localized biological response of the body to the implant. The tissue response modifier is nonsurgically delivered from the delivery system into the body in a quantity effective to direct the localized biological response of the body to the implant. The invention also provides an implant system for long-term use comprising an implant and nonsurgical means for delivering a tissue response modifier through the epidermis of the body, the tissue response modifier effective for directing a localized biological response of the body to the implant.

22 Claims, 3 Drawing Sheets

(56) References Cited

U.S. PATENT DOCUMENTS

| | | | |
|---|---|---|---|
| 6,011,984 A | 1/2000 | Van Antwerp et al. | |
| 6,013,122 A | 1/2000 | Klitzman et al. | |
| 6,040,194 A | 3/2000 | Chick et al. | |
| 6,212,416 B1 | 4/2001 | Ward et al. | |
| 6,299,604 B1 | 10/2001 | Ragheb et al. | |
| 6,475,750 B1 | 11/2002 | Han et al. | |
| 6,497,729 B1 | 12/2002 | Moussy et al. | |
| 6,642,015 B2 | 11/2003 | Vachon et al. | |
| 6,671,527 B2 | 12/2003 | Petersson et al. | |
| 6,702,857 B2 | 3/2004 | Brauker et al. | |
| 6,794,195 B2 | 9/2004 | Colvin, Jr. | |
| 6,804,544 B2 | 10/2004 | Van Antwerp et al. | |
| 6,818,226 B2 | 11/2004 | Reed et al. | |
| 6,844,023 B2 | 1/2005 | Schulman et al. | |
| 6,965,791 B1 | 11/2005 | Hitchcock et al. | |
| 7,060,503 B2 | 6/2006 | Colvin, Jr. | |
| 7,067,194 B2 | 6/2006 | Mao et al. | |
| 7,110,803 B2 | 9/2006 | Shults et al. | |
| 7,132,049 B2 | 11/2006 | Hou et al. | |
| 7,134,999 B2 | 11/2006 | Brauker et al. | |
| 7,153,265 B2 | 12/2006 | Vachon | |
| 7,162,289 B2 | 1/2007 | Shah et al. | |
| 7,186,789 B2 | 3/2007 | Hossainy et al. | |
| 7,192,450 B2 | 3/2007 | Brauker et al. | |
| 7,202,947 B2 | 4/2007 | Liu et al. | |
| 7,226,978 B2 | 6/2007 | Tapsak et al. | |
| 7,228,159 B2 | 6/2007 | Petersson et al. | |
| 7,939,332 B2 | 5/2011 | Colvin, Jr. | |
| 7,972,628 B2 | 7/2011 | Ratner et al. | |
| 8,318,193 B2 | 11/2012 | Ratner et al. | |
| 8,372,423 B2 | 2/2013 | Marshall et al. | |
| 8,647,393 B2 | 2/2014 | Marshall et al. | |
| 8,666,471 B2 | 3/2014 | Rogers | |
| 2002/0043651 A1 | 4/2002 | Darrow et al. | |
| 2002/0048577 A1* | 4/2002 | Bornstein | A61K 38/19 424/94.63 |
| 2002/0193672 A1 | 12/2002 | Walsh et al. | |
| 2003/0004554 A1* | 1/2003 | Riff et al. | 607/62 |
| 2003/0088682 A1 | 5/2003 | Hlasny | |
| 2003/0099682 A1 | 5/2003 | Moussy et al. | |
| 2003/0171666 A1 | 9/2003 | Loeb et al. | |
| 2003/0208166 A1 | 11/2003 | Schwartz | |
| 2004/0106951 A1 | 6/2004 | Edman et al. | |
| 2004/0143221 A1 | 7/2004 | Shadduck | |
| 2004/0176669 A1 | 9/2004 | Colvin, Jr. | |
| 2004/0195528 A1 | 10/2004 | Reece et al. | |
| 2005/0027175 A1 | 2/2005 | Yang | |
| 2005/0096587 A1* | 5/2005 | Santini, Jr. | A61B 5/4839 604/66 |
| 2005/0119737 A1 | 6/2005 | Bene | |
| 2005/0154374 A1* | 7/2005 | Hunter et al. | 604/890.1 |
| 2005/0182389 A1* | 8/2005 | LaPorte et al. | 604/890.1 |
| 2005/0245799 A1 | 11/2005 | Brauker et al. | |
| 2006/0002969 A1 | 1/2006 | Kyriakides et al. | |
| 2006/0089548 A1 | 4/2006 | Hogan | |
| 2006/0252976 A1 | 11/2006 | Rosero | |
| 2006/0275340 A1 | 12/2006 | Udipi et al. | |
| 2006/0289307 A1 | 12/2006 | Yu et al. | |
| 2007/0010702 A1 | 1/2007 | Wang | |
| 2007/0093617 A1 | 4/2007 | DesNoyer et al. | |
| 2007/0105176 A1* | 5/2007 | Ibey | C12Q 1/54 435/14 |
| 2007/0134290 A1 | 6/2007 | Rowland et al. | |
| 2007/0135698 A1 | 6/2007 | Shah et al. | |
| 2007/0244379 A1 | 10/2007 | Boock et al. | |
| 2007/0270675 A1 | 11/2007 | Kane et al. | |
| 2008/0020012 A1 | 1/2008 | Ju et al. | |
| 2008/0139903 A1 | 6/2008 | Bruce et al. | |
| 2009/0131773 A1 | 5/2009 | Struve et al. | |
| 2009/0221891 A1 | 9/2009 | Yu et al. | |
| 2010/0123121 A1 | 5/2010 | Taylor | |
| 2010/0160749 A1 | 6/2010 | Gross et al. | |
| 2011/0028806 A1 | 2/2011 | Merritt et al. | |
| 2012/0140094 A1 | 6/2012 | Shpunt et al. | |
| 2012/0265034 A1 | 10/2012 | Wisniewski et al. | |
| 2013/0006069 A1 | 1/2013 | Gil et al. | |
| 2013/0158413 A1 | 6/2013 | Lisogurski et al. | |
| 2013/0211212 A1 | 8/2013 | Stumber | |
| 2013/0211213 A1 | 8/2013 | Dehennis et al. | |
| 2013/0213110 A1 | 8/2013 | Papadimitrakopoulos et al. | |
| 2013/0229660 A1 | 9/2013 | Goldschmidt et al. | |
| 2014/0275869 A1 | 9/2014 | Kintz et al. | |
| 2014/0357964 A1 | 12/2014 | Wisniewski et al. | |
| 2014/0364707 A1 | 12/2014 | Kintz et al. | |

FOREIGN PATENT DOCUMENTS

| | | |
|---|---|---|
| WO | 91/09312 A1 | 6/1991 |
| WO | 97/19188 A1 | 5/1997 |
| WO | 98/06406 A1 | 2/1998 |
| WO | 00/02048 A1 | 1/2000 |
| WO | WO 02/087610 A1 | 11/2002 |
| WO | WO 03/006992 | 1/2003 |
| WO | 2005/120631 A1 | 12/2005 |
| WO | WO 2006004595 A2 * | 1/2006 |
| WO | WO 2006/130461 | 12/2006 |
| WO | WO 2007/126444 | 11/2007 |
| WO | WO 2008/141241 | 11/2008 |
| WO | WO 2008/143651 | 11/2008 |
| WO | WO 2010/037847 | 4/2010 |
| WO | WO 2013/132400 | 9/2013 |

OTHER PUBLICATIONS

Garg, S.K, et al. Improved glucose excursions using an implantable real-time continuous glucose sensor in adults with Type 1 diabetes. Diabetes Care. 2004. 27(3): 734-738.

Henninger, N., et al. Tissue response to subcutaneous implantation of glucose-oxidase-based glucose sensors in rats. Biosens Bioelectron. 2007. 23(1):26-34.

Klimowicz, A., et al. Evaluation of skin penetration of topically applied drugs by cutaneous microdialysis:acyclovir vs salicylic acid. J Clin Pharm Ther 3(2):143-148.

Smith, J.L., "The Pursuit of Noninvasive Glucose: 'Hunting the Deceitful Turkey'"; 2006.

Bardwaj, U., et al. A review of the development of a vehicle for localized and controlled drug delivery for implantable biosensors. J Diab Science and Tech. 2008 2(6):1016-1029.

Onuki, Y., et al. A review of the biocompatibility of implantable devices: Current challenges to overcome foreign body response. J Diab Science and Tech. 2008 2(6):1003-1015.

Nagler, A., et al. Topical treatment of cutaneous chronic graft versus host disease with halofuginone: a novel inhibitor of collagen Type 1 Synthesis. Transplantation. 1999. 68(11):1806-1809.

Pickup, J.C., et al. In vivo glucose monitoring: the clinical reality and the promise. Biosens Bioelectron. 2005. 20(10): 1897-1902.

Vilavalur, R., et al. Sildenafil induces angiogenic response in human coronary arteriolor endothelial cells through the expression of thioredoxin, hemaoxygenase, and VEGF. 2006 Vasc Pharm 45(2):91-95.

Ward, W.K., et.al. The effect of microgeometry, implant thickness and polyurethane chemistry on the foreign body response to subcutaneous implants. Biomaterials. 2002. 23(21:4185-4192.

Wisniewski, N., et. al. Methods for Reducing Biosensor Membrane Biofouling. Colloids and Surfaces B: Biointerfaces. 2000. 18:197-219.

Wisniewski, N, et.al. Characterization of implantable biosensor membrane fouling. Fresen J Anal Chem. 2000. 366 (6-7):611-621.

Woderer, S. Continuous glucose monitoring in interstitial fluid using glucose oxidase-based sensor compared to established blood glucose measurement in rats. Anal Chim Acta. Jan. 2, 2007;581(1):7-12. Epub Aug. 18, 2006.

Australian Examination Report in Application No. AU 2010256930, dated Dec. 18, 2013.

Australian Examination Report in Application No. AU 2010256930, dated Oct. 28, 2014.

Australian Examination Report in Application No. AU 2010256930, dated Feb. 13, 2015.

(56) References Cited

OTHER PUBLICATIONS

Chinese Office Action and Search Report in Application No. CN 201080033712.3, dated Jan. 5, 2013 (and English translation).
Chinese Office Action in Application No. CN 201080033712.3, dated Sep. 23, 2013 (and English translation).
Japanese Office Action in Application No. JP 2012-514023, dated Mar. 10, 2014 (and English translation).
Japanese Office Action in Application No. JP 2012-514023, dated Dec. 22, 2014 (and English translation).
International Search Report in International Application No. PCT/US2010/036698, dated Feb. 9, 2011.
International Preliminary Report on Patenability in International Application No. PCT/US2010/036698, dated Dec. 6, 2011.
Office Action for Canadian Application No. 2,763,687, dated Aug. 5, 2015.
Supplementary European Search Report for European Patent Application No. 10783874.0, mailed Aug. 25, 2015.
Alexeev et al., "High ionic strength glucose-sensing protonic crystal," Anal. Chem., 75:2316-2323 (2003).
Alexeev et al., "Protonic crystal glucose-sensing material for non-invasive monitoring of glucose in tear fluid," Clinical Chemistry, 50(12):2353-2360 (2004).
Aslan et al., "Nanogold plasmon-resonance-based glucose sensing 2: wavelengthratiometric resonance light scattering," Anal. Chem., 77(7):2007-2014 (2005).
Badylak et al., "Immune response to biologic scaffold materials," Seminars in Immunology, 20(2):109-116 (2008).
Ballerstadt et al., "Competitive-binding assay method based on fluorescence quenching of ligands held in close proximity by a multivalent receptor," Anal. Chem., Acta. 345:203-212 (1997).
Billingsley et al., "Fluorescent nano-optodes for glucose detection," Anal. Chem., 82(9):3707-3713 (2010).
Brasuel et al., "Fluorescent nanosensors for intracellular chemical analysis: decyl methacrylate liquid polymer matrix and ion-exchange-based potassium pebble sensors with real-time application to viable rat C6 glioma cells," Anal. Chem., 73(10):2221-2228 (2001).
Brasuel et al., "Liquid polymer nano-pebbles for CL—analysis and biological applications," Analyst, 128(10):1262-1267 (2003).
Braun et al., "Comparison of tumor and normal tissue oxygen tension measurements using oxylite or microelectrodes in rodents," Am. J. Physiol. Heart Circ. Physiol., 280(6):H2533-H2544 (2001).
Bridges et al., "Chronic inflammatory responses to microgel-based implant coatings," J Biomed. Mater. Res. A., 94(1):252-258 (2010).
Chaudhary et al., "Evaluation of glucose sensitive affinity binding assay entrapped in fluorescent dissolved-core alginate microspheres," Biotechnology and Bioengineering, 104(6):1075-1085 (2009).
Dunphy, I. et al., "Oxyphor R2 and G2: phosphors for measuring oxygen by oxygen-dependent quenching phosphorescence," Anal. Biochem., 310:191-198 (2002).
Horgan et al., "Crosslinking of phenylboronic acid receptors as a means of glucose selective holographic detection," Biosensors and Bioelectronics, 21(9):1838-1845 (2006).
Ibey et al., "Competitive binding assay for glucose based on glycodendrimer fluorophore conjugates," Anal. Chem., 77(21):7039-7046 (2005).
Isenhath et al., "A mouse model to evaluate the interface between skin and a percutaneous device," J Biomed. Mater. Research, 83A:915-922 (2007).
Ju, Y. M. et al., "A novel porous collagen scaffold around an implantable biosensor for improving biocompatibility. I. In vitorl in vivo stability of the scaffold and in vitro sensitivity of the glucose sensor with scaffold," J Biomed. Mater. Research, 87A:136-146 (2008), Available online Dec. 17, 2007.
Kaehr et al., "Multiphoton fabrication of chemically responsive protein hydrogels for microactuation," PNAS USA, 105(26):8850-8854 (2008).

Kasprzak, S. E., "Small-scale polymer structures enabled by thiol-ene copolymer systems," Doctoral Dissertation, Georgia Institute of Technology, May 2009.
Kloxin, A. M. et al., "Photodegradable hydrogels for dynamic tuning of physical and chemical properties," Science, 324:59-63 (2009).
Mansouri et al., "A minature optical glucose sensor based on affinity binding," Nature Biotechnology, 23:885-890 (1984).
Marshall et al., "Biomaterials with tightly controlled pore size that promote vascular in-growth," ACS Polymer Preprints, 45(2):100-101 (2004).
McShane et al., "Glucose monitoring using implanted fluorescent microspheres," IEEE Engineering in Medicine and Biology Magazine, 19(6):36-45 (2000).
Nielsen et al., "Clinical evaluation of a transcutaneous interrogated fluorescence lifetime-based microsensor for continuous glucose reading," J Diabetes and Technology, 3(1):98-109 (2009).
Nielson, R. et al., "Microreplication and design of biological architectures using dynamicmask multiphoton lithography," Small, 5(1):120-125 (2009).
Ostendorf, A. et al., "Two-photon polymerization: a new approach to micromachining," Photonics Spectra, 40(10):72-79 (2006).
Ozdemir et al., "Axial pattern composite prefabrication of high-density porous polyethylene: experimental and clinical research," Plast. Reconstr. Surg., 115(1):183-196 (2005).
Phelps et al., "Bioartificial matrices for therapeutic vascularization," PNAS USA, 107(8):3323-3328 (2010).
Rounds et al., "Microporated peg spheres for fluorescent analyte detection," Journal of Fluorescence, 17(1):57-63 (2007), Available online Nov. 17, 2006.
Russell et al., "A fluorescence-based glucose biosensor using concanavalin A and dextran encapsulated in apoly(ethylene glycol) hydrogel," Anal. Chem., 71(15):3126-3132 (1999).
Sanders et al., "Tissue response to single-polymer fibers of varying diameters: evaluation of fibrous encapsulation and macrophage density," J Biomed. Mater. Research, 52:231-237 (2000).
Sanders et al., "Tissue response to microfibers of different polymers: polyester, polyethylene, polylactic acid, and polyurethane," J Biomed. Mater. Research, 62(2):222-227 (2002).
Sanders et al., "Fibrous encapsulation of single polymer microfibers depends on their vertical dimension in subcutaneous tissue," J Biomed. Mater. Research, 67A:1181-1187 (2003).
Sanders et al., "Relative influence of polymer fiber diameter and surface charge on fibrous capsule thickness and vessel density for single-fiber implants," J Biomed. Mater. Research, 65A:462-467 (2003).
Sanders et al., "Polymer microfiber mechanical properties: a system for assessment and investigation of the link with fibrous capsule formation," J Biomed. Mater. Research, 67A:1412-1416 (2003).
Sanders et al., "Small fiber diameter fibro-porous meshes: tissue response sensitivity to fiber spacing," J Biomed Mater Research, 72A:335-342 (2005).
Sanders et al., "Fibro-porous meshes made from polyurethane micro-fibers: effects of surface charge on tissue response," Biomaterials, 26(7):813-818 (2005).
Schultz et al., "Affinity sensor: a new technique for developing implantable sensors for glucose and other metabolites," Diabetes Care, 5(3)245-253 (1982).
Srivastava et al., "Application of self-assembled ultrathin film coatings to stabilize macromolecule encapsulation in alginate microspheres," J of Microencapsulation, 22(4):397-411 (2005).
Srivastava et al., "Stabilization of glucose oxidase in alginate microspheres with photo reactive diazoresin nanofilm coatings," Biotechnology and Bioengineering, 91(1):124-131 (2005).
Takano et al., "An oxo-bacteriochlorin derivative for long-wavelength fluorescence ratiometric alcohol sensing," Analyst, 135:2334-2339 (2010).
Tian et al., "Dually fluorescent sensing of PH and dissolved oxygen using a membrane made from polymerizable sensing monomers," Sensors and Actuators B, 147:714-722 (2010).
Tian et al., "Influence of matrices on oxygen sensing of three-sensing films with chemically conjugated platinum porphyrin (56) References Cited

OTHER PUBLICATIONS probes and preliminary application for monitoring of oxygen consumption of *Escherichia coli* (*E coli*)." Sensors and Actuators B 150:579-587 (2010).

Tian, Y. et al., "A New Cross-linkable Oxygen Sensor Covalently Bonded into Poly(2-hydroxyethyl methacrylate)-co-Polyacrylamide Thin Film for Dissolved Oxygen Sensing," Chem. Mater, 22:2069-2078 (2010).

Shibata, H. et al., "Injectable hydrogel microbeads for fluorescence-based in vivo continuous glucose monitoring", Proceedings of the National Academy of Sciences of the United States of America, Oct. 19, 2010, vol. 107, No. 42, pp. 17894-17898.

Young et al., "A novel porous collagen scaffold around an implantable biosensor for improving biocompatibility. I. In vitro/in vivo stability of the scaffold and in vitro sensitivity of the glucose sensor with scaffold," Journal of Biomedical Materials Research Part A., 2008, vol. 87, pp. 136-146.

\* cited by examiner

METHOD AND SYSTEM FOR DIRECTING A LOCALIZED BIOLOGICAL RESPONSE TO AN IMPLANT

CROSS-REFERENCE TO RELATED APPLICATIONS

This application claims the benefit of U.S. Provisional Application No. 61/182,995 filed Jun. 1, 2009, the disclosure of which is herein incorporated by reference.

TECHNICAL FIELD

This invention relates generally to implants. More specifically, the invention relates to methods for directing a localized biological response of a mammalian body to an implant disposed within the body and to an implant system for long-term use.

BACKGROUND OF THE INVENTION

Methods have long been sought for extending the useful life of an implant that is inserted into the body. Not only is it important for an implant to last long enough to justify the cost, potential complications, and pain of implantation, but many situations exist in which there are strong medical reasons for maintaining the same implant within the body for an extended period of time. For example, when the implant is a sensor, having reliable, consistent, and continuous data from the same sensor can improve patient care.

Studies have shown that continuous measurement of biochemical analytes or drugs in the body significantly improves management and treatment of acute or chronic illnesses. For example, continuous monitoring may provide better control of diabetes, reducing the incidence of sequelae that lead to vision loss and impaired circulation. In trauma and congestive heart failure patients, the levels of lactate and glucose should be monitored simultaneously and continuously to facilitate detection of occult bleeding and changes in shock status. Real-time monitoring over the course of systemic administration of drugs or chemotherapeutic agents that have narrow ranges of effective concentration can provide the clinician with feedback upon which to make adjustments to dosing to assure proper concentrations are achieved and maintained.

Over a period of more than 20 years, many attempts have been made to develop an implanted sensor that provides frequent or continuous monitoring. For example, U.S. Pat. No. 4,703,756 to Gough et al., filed May 6, 1986, describes a sensor module for implantation in the body to monitor glucose and oxygen levels. When a sensor (or any other foreign body) is implanted, inflammatory and immune responses are initiated. Within minutes, protein (primarily fibrinogen) and platelets begin to adhere to the implant, followed over hours to days by recruitment of inflammatory and immune cells, which then surround the sensor. These initial tissue responses result in protein fouling of the sensor interface and potential degradation of the sensor chemistry by enzymes. Over the subsequent days and weeks, granulation tissue forms as the body attempts to repair the tissue damaged by the implantation procedure. Eventually, continued collagen production over the following weeks to months leads to formation of an avascular capsule surrounding the sensor and causes loss of analyte availability to the sensor. The avascular capsule is believed to be ultimately responsible for the majority of the drift of signal, loss of sensor sensitivity, and the need for frequent recalibration or even sensor replacement.

Various technologies have attempted to overcome this problem. For example, sensors have been developed that are placed intravascularly to avoid the problems of a capsule by allowing the tip of the sensor to be in continuous contact with the blood. However, placing a sensor directly into the vasculature puts the recipient at risk for thrombophlebosis, thromboembolism, and thrombophlebitis.

Sensors have also been developed that have physical features designed to address the problem of the foreign body response. For example, U.S. Pat. No. 6,212,416 to Ward et al. and U.S. Pat. No. 7,134,999 to Brauker et al. both offer architectural solutions. Ward et al. describe a movable outer membrane that can be renewed when it becomes fouled. Brauker et al. describe a sensor having a geometric design intended to minimize chronic inflammatory response at the sensing region of the sensor. However, these solutions do not permit the device to remain fully functional for long-term use, i.e., over a period of months or even years.

Attempts have been made to control the foreign body response by implanting therapeutic agents, e.g., tissue response modifiers, at the same time as the sensor. Such tissue response modifiers attempt to mask the presence of the implant within the body and reduce or eliminate the foreign body response. Vachon, in U.S. Pat. No. 6,212,416, describes a biosensor comprising an accessory material that includes a coating containing a hydrophilic material and/or a fiber modified to deliver a therapeutic agent. In U.S. Pat. No. 6,497,729, Moussey et al. describe a tissue/implant interface comprising a polymer layer that contains at least one tissue response modifier covalently attached to the polymer layer or entrapped within the polymer layer.

Such devices are successful in directing the foreign body response for a period of time that is limited by the amount of therapeutic agent that can be delivered along with the sensor. The mass of a drug or other compound necessary to consistently control the foreign body response over a period of 2-5 years is on the scale of hundreds to thousands of milligrams. This quantity is too large for a one-time administration or for incorporation into a drug reservoir feature of the sensor. Because the foreign body response increases when the size of the implant increases, delivering a sensor made larger by its accompanying therapeutic agent would be counterproductive. Furthermore, even if means were conceived to achieve a one-time delivery of a large quantity of a therapeutic agent, no known drugs or compounds for controlling a foreign body response are capable of remaining stable at body temperatures of 35° C. to 37° C. over a period of 2-5 years.

Therefore, it would be desirable to have an improved method for directing a localized biological response of a mammalian body to an implant and an implant system for long-term use that overcome the aforementioned and other disadvantages.

SUMMARY OF THE INVENTION

One aspect of the present invention is a method for directing a localized biological response of a mammalian body to an implant disposed within the body. A first delivery system is positioned outside the body and adjacent to the implant. The delivery system comprises a tissue response modifier effective for directing a localized biological response of the body to the implant. The tissue response modifier is delivered from the delivery system into the body in a quantity effective to direct the localized biological response of the body to the implant. Delivery of the tissue response modifier into the body is nonsurgical.

Another aspect of the present invention is a method for directing a localized biological response of a mammalian body to an implant. A delivery system is positioned outside the body adjacent to a location within the body identified for receiving the implant. The delivery system comprises a tissue response modifier effective for directing a localized biological response of the body to the implant. The tissue response modifier is delivered from the delivery system into the body in a quantity effective to direct a localized biological response of the body. Delivery of the tissue response modifier into the body is nonsurgical.

Yet another aspect of the present invention is an implant system for long-term use within a mammalian body. The system comprises an implant and nonsurgical means for delivering a tissue response modifier through the epidermis of the mammalian body, the tissue response modifier effective for directing a localized biological response of the body to the implant.

The aforementioned and other features and advantages of the invention will become further apparent from the following detailed description read in conjunction with the accompanying drawings, which are not to scale. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
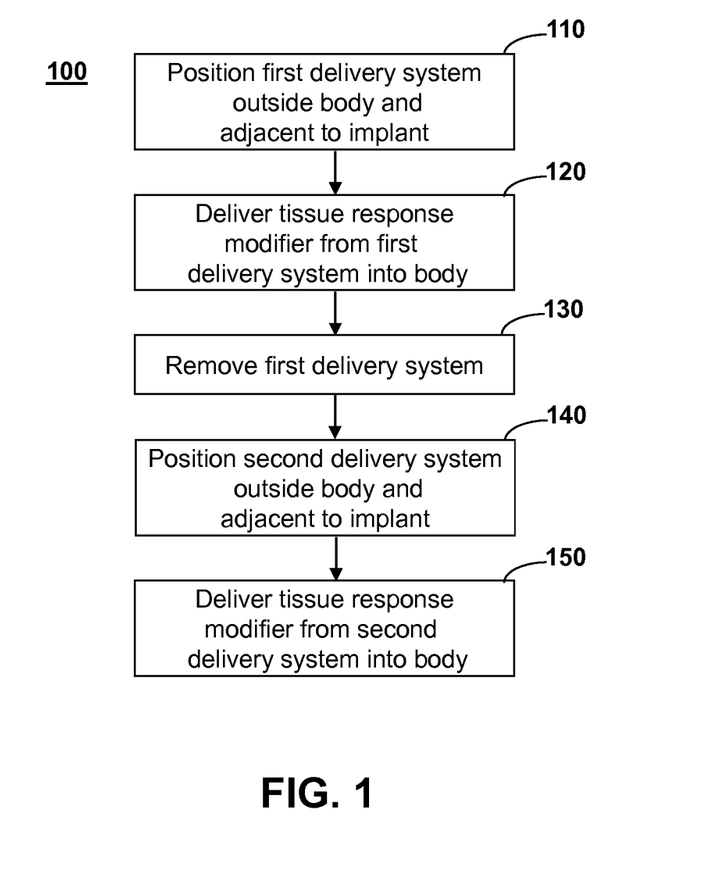
FIG. 1 is a flow diagram of one embodiment of a method for directing a localized biological response of a mammalian body to an implant disposed within the body, in accordance with the present invention, in which the method is used to prolong the useful life of the implant.

One aspect of the present invention is a method for directing a localized biological response of a mammalian body to an implant disposed within the body. FIG. 1 shows a flow diagram of one embodiment of the method in accordance with the present invention.

In the present embodiment, the implant is disposed within the mammalian body adjacent to an outside surface of the body. For example, the implant may be disposed in one or more of the hypodermis, the subcutis, the subcutaneous adipose fat, the dermis, an intradermal location, and a subdermal location. In one embodiment, the implant is positioned such that it is fully enclosed within the mammalian body.

The implant may be any device or material disposed in or under the skin. For example, the implant may be a sensor (e.g., analyte, electrical, mechanical, and/or thermal sensor), a drug delivery device, a pump, a chip, combinations thereof, and the like. Typically the mammalian body is allowed to stabilize for an appropriate period of time following insertion of the implant before carrying out the method. The time may be minimal where the implant is delivered via a syringe or catheter, or as long as several days where the implant is delivered surgically.

In the present embodiment, a tissue response modifier (comprising one or more individual modifiers) is delivered into the body in a quantity effective to direct a localized biological response of the body to the implant, thereby prolonging the useful life of the implant. As used herein, the terms "direct" and "directing" denote both reducing and increasing various aspects of the localized biological response as well as eliminating various aspects altogether.

In the method shown at 100, a first delivery system is positioned outside the mammalian body adjacent to the implant (Block 110). The first delivery system may comprise one or more of a cream, a gel, an ointment, a sprayer, a patch, a bandage insert, an array of microneedles, a syringe, and the like. The delivery system may also comprise one or more of a radiation source (e.g., a source of light, ultrasound, electricity, magnetism, heat, and/or cooling) and a pressure source (used, for example, for laser-induced pressure delivery).

Where the delivery system is a patch or a bandage insert, positioning the delivery system outside the body and adjacent to the implant involves applying the patch or bandage insert to an outside surface of the body adjacent to the implant (e.g., to the epidermis in the area of the body within which the implant resides). Positioning a cream, a gel, an ointment, or another similar preparation that delivers a tissue response modifier transdermally (i.e., through unbroken skin) involves applying the preparation to an outside surface of the body. Where the delivery system is, for example, a sprayer or a syringe, positioning the delivery system outside the body adjacent to the implant involves placing the system in position to spray material onto the skin or inject material into or through the skin. A radiation source or pressure source would be placed in position to allow delivery of the radiation or pressure to skin tissue adjacent to the implant.

The delivery system comprises a tissue response modifier effective for directing a localized biological response of the body to the implant. As defined herein, the term "tissue response modifier" denotes a substance or physical phenomenon that increases, decreases, or eliminates one or more aspects of the tissue response. In the present embodiment, the tissue response modifier is selected to prevent or minimize a biological response that would impede availability of analyte to the implant or otherwise limit the useful life of the implant, or to increase a biological response that would prolong the useful life of the implant.

The tissue response modifier may comprise, for example, one or more of a collagen inhibitor, an anti-fibrotic agent, an angiogenic agent, a vasculogenic agent, a pro-vascular dilation agent, an immunosuppressive agent, an anti-proliferative agent, an anti-migratory agent, an anti-inflammatory agent, a vasodilator, an anti-histamine, an anti-protein-fouling agent, a synthetic molecule, a biologically produced molecule, a permeation enhancer, a gene therapy agent, a stem cell, a mammalian cell, a drug, and the like. The tissue response modifier may also comprise visible light, other wavelengths of light, ultrasound, heat, an electrical pulse, a magnetic field, a magnetic pulse, and combinations thereof.

Specific examples of tissue response modifiers include aspirin, imatinib, celecoxib, rofecoxib, etoricoxib, transforming growth factor β3, interleukin 10, mannose-6-phosphate, cortisone, prednisone, dexamethasone, ibuprofen, cromolyn sodium, halofuginone hydrobromide, tranilast, perfenidone, D-penicillamine, 1-butyryl-glycerol, adenosine, methrotrexate, mycophenolate mofetil, tacrolimus, paclitaxel, rapamycin, doxorubicin, azathioprene, losartan potassium, mitomycin C, diclofenac, dexamethasone, ketoprofane, prostscylin, nifedipine, loratadine, nedocromil, detergents, tissue necrosis factors and/or their inhibitors, platelet derived growth factor, portions of these molecules, sense or anti-sense molecules, and combinations thereof. The above lists are not intended to be exhaustive; additional, unnamed tissue response modifiers are anticipated to be effective in the claimed methods.

The tissue response modifier is delivered from the delivery system into the body in a quantity effective to direct the localized biological response of the body to the implant (Block 120). The tissue response modifier may be delivered transdermally (through unbroken skin) and/or may be injected into the body through skin tissue adjacent to the implant.

For example, the delivery system may be a patch that includes a tissue response modifier that diffuses into the body through the epidermis and onto and/or around the implant. Alternatively or additionally, the patch may include an array of microneedles, with the tissue response modifier injected by the microneedles into skin tissue adjacent to the implant. The tissue response modifier may also be delivered transdermally via a cream, gel, ointment or sprayer or may be injected into the area of the implant using a hypodermic needle, a catheter, or another injection device, taking care to avoid the implant.

The tissue response modifier is not delivered from the delivery system surgically, i.e., it is not delivered via an incision, nor is the material contained in the delivery system delivered along with the implant at the same time the implant is inserted into the body. In the present method, the tissue response modifier is delivered separately from and later than the implant.

The tissue response modifier is delivered at a low level (e.g., at a low dosage) because the tissue response modifier is not intended to reach systemic levels but is intended to reach adequate local levels to direct the biological response of the localized tissue of the body to the implant. The tissue response modifier is supplied in a quantity effective to direct the tissue architecture, vascularity, collagen content, protein deposition, cellular activity, and/or other tissue characteristics at the tissue-implant interface and up to several centimeters away from the implant. This quantity is low compared to the typically delivered system doses. For example, aspirin, an anti-inflammatory and anti-platelet molecule working by means of cycloxygenase inhibition, is typically delivered systemically at a therapeutic level of 325 mg aspirin/80 kg body weight. Local delivery doses of aspirin to the region of a typically sized electrochemical sensor implant would be approximately 1,000 to 10,000 times less in dosage than systemically delivered doses administered to achieve the same local concentrations.

Delivery of the tissue response modifier may be aided by processes such as electroporation, iontophoresis, sonophoresis, laser-induced pressure, delivery of permeation enhancers, and the like. The delivery system may include, in addition to the tissue response modifier, a material effective to target delivery of the tissue response modifier to a specific location within the body and/or to modulate uptake of the tissue response modifier by the body. For example, cell-specific adhesion molecules or other specific adhesion molecules (e.g., to target adhesion to collagen or proteoglycans in the interstitial space) may be included along with the tissue response modifier to achieve targeted delivery of the tissue response modifier to a specific location such as the dermis or subcutis. In other alternatives, the material may modulate uptake into the bloodstream, into specific cell types, into specific structures (e.g., collagen bundles) and/or into or through the epidermis, dermis, and or subcutaneous.

In addition to materials or functions related to delivery of the tissue response modifier, the delivery system may also include components related to activities of the implant. For example, where the implant is a device (e.g., a sensor or a pump), the delivery system may include one or more components such as an illuminator, a detector, a signal receiver, a signal transmitter, an energy storage component, a data storage component, and the like.

In the present embodiment, in which the localized biological response of the body to the implant is being directed in order to prolong the useful life of the implant, typically a second (third, fourth, etc.) delivery system is utilized. Before the tissue response modifier provided by the first delivery system loses its effectiveness, the second delivery system is positioned outside the body and adjacent to the implant (Block 140), and the second tissue response modifier is delivered from the second delivery system into the body (Block 150). The second delivery system may include the same or a different tissue response modifier (comprising one or more individual modifiers) effective for directing the localized biological response of the body to the implant. The second tissue response modifier, like the first, is delivered nonsurgically.

The first delivery system may be removed (Block 130) prior to positioning the second delivery system. For example, where the delivery system comprises a patch, the first patch would be removed prior to positioning a second patch. Where the first delivery system is a topical preparation such as a cream, the cream need not be washed off before a second tissue response modifier is delivered. Typically a second delivery system will comprise the same tissue response modifier as the first system, but an advantage of delivering the tissue response modifier from outside the body is that the tissue response modifier and/or its mode of delivery can be changed or combined with another tissue response modifier and/or mode of delivery to optimally direct the body's response to the implant.

Figure 2:
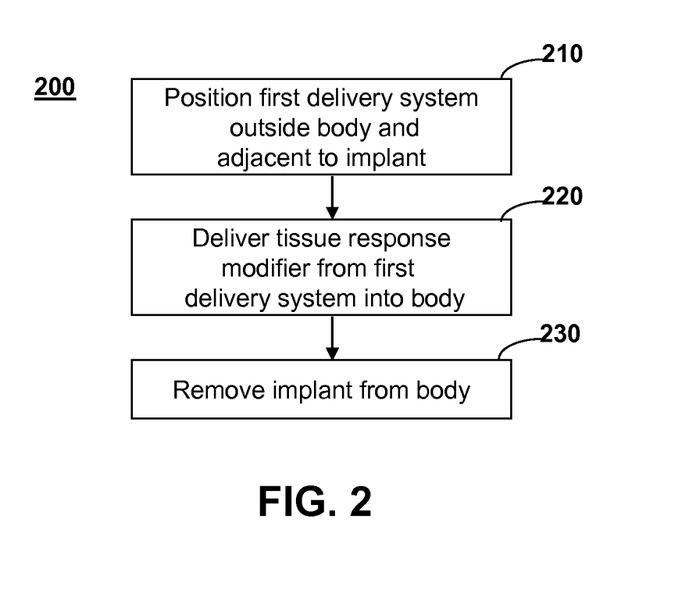
FIG. 2 is a flow diagram of another embodiment of a method for directing a localized biological response of a mammalian body to an implant disposed within the body, in accordance with the present invention, in which the method is used to facilitate removal of the implant.

FIG. 2 shows a flow diagram of another embodiment of a method for directing a localized biological response of a mammalian body to an implant disposed within the body, in accordance with the present invention. In this embodiment, a tissue response modifier is delivered into the body in a quantity effective to direct a localized biological response of the body to the implant to aid in preparing the body and/or the implant for removal of the implant.

In the method shown at 200, a first delivery system, comprising a first tissue response modifier effective for directing a localized biological response of the body to the implant, is positioned outside the mammalian body adjacent to the implant (Block 210). The first delivery system may be as described above for method 100, with the tissue response modifier selected for facilitating removal of the implant.

The tissue response modifier is delivered from the first delivery system into the body in a quantity effective to direct the localized biological response of the body to the implant (Block 220). Delivery of the tissue response modifier may be carried out as described above for method 100. The present embodiment will find particular utility where the localized biological response of the body to the implant has not been directed during the tenure of the implant within the body as in the embodiment described above and illustrated at 100. For example, the tissue response modifier in this embodiment may be a drug or other treatment intended to reduce vascularization in the area of the implant to reduce bleeding during its removal. It may also be a drug or other treatment effective to reduce collagen buildup surrounding the implant to limit the amount of tissue that will be removed along with the implant.

At some time after the tissue response modifier has been delivered from the first delivery system into the body, the implant is removed from the body (Block 230), typically by surgical means (i.e., an incision is made in the body, and the implant is removed through the incision). It is anticipated that a second (third, fourth, etc.) delivery system may be used as needed prior to removal of the implant.

Figure 3:
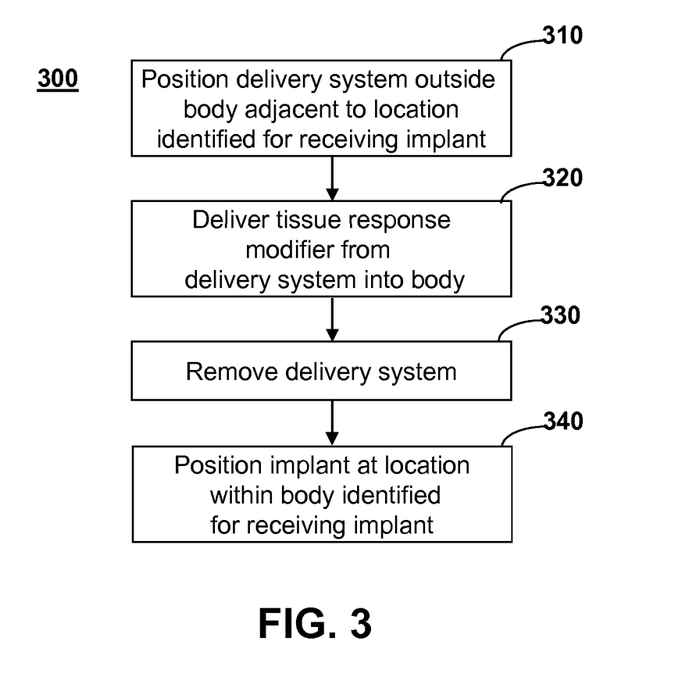
FIG. 3 is a flow diagram of a method for directing a localized biological response of a mammalian body, in accordance with the present invention, in which the method is used to aid in preparing the body for an implant.

FIG. 3 shows a flow diagram of one embodiment of a method for directing a localized biological response of a mammalian body to an implant, in accordance with the present invention, in which the method is used to aid in preparing the mammalian body for insertion of an implant.

In the method shown at 300, a first delivery system, comprising a first tissue response modifier effective for directing a localized biological response of the body to the implant, is positioned outside the mammalian body adjacent to a location within the body identified for receiving the implant (Block 310). The first delivery system may be as described above for method 100.

The tissue response modifier is delivered from the delivery system into the body in a quantity effective to direct the localized biological response of the body to the implant (Block 320). Delivery of the tissue response modifier is nonsurgical and may be carried out as described above for method 100.

The delivery system is removed (Block 330) as needed, and the implant is positioned at the location within the body identified for receiving the implant (Block 340). By delivering a tissue response modifier into the body in advance of the implant, a localized biological response of the body to the implant may be directed to minimize or avoid an undesirable response of the body to the implant or to initiate or enhance a desired response.

In an alternative embodiment, a material that attracts and/or contains the tissue response modifier may be implanted within the body adjacent to the implant, and the tissue response modifier may then be delivered into the implanted material. In the case of a tissue response modifier delivered transdermally or using microneedles, the tissue response modifier would diffuse into and pool within the implanted material. In the case of a tissue response modifier injected using a hypodermic needle or a catheter, the tissue response modifier could be injected directly into the implanted material. The implanted material serves as a reservoir for the tissue response modifier, allowing it to be released into the area of the implant over time.

Figure 4:
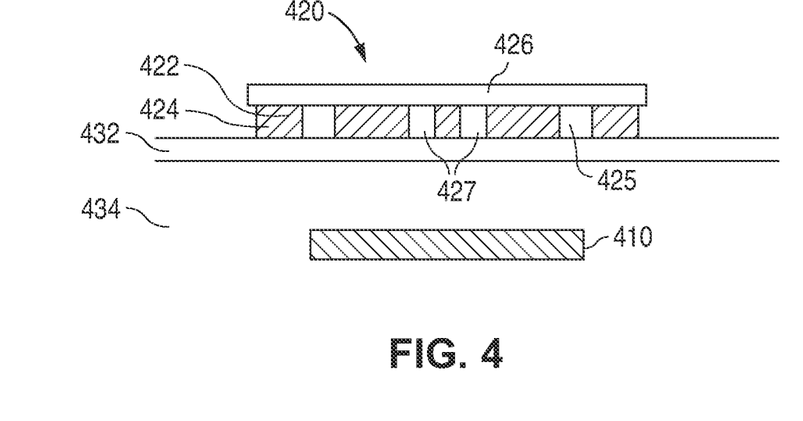
FIG. 4 is an illustration of one embodiment of an implant system for long-term use, in accordance with the present invention, the exemplary implant shown as a sensor, and the exemplary nonsurgical means for delivering a tissue response modifier shown as a patch.

Another aspect of the present invention is an implant system for long-term use within a mammalian body. One embodiment of the system, in accordance with the present invention, is illustrated in FIG. 4, which shows a cross-section view of an implant 410 disposed within the body and nonsurgical delivery means 420 disposed outside the body for delivering a tissue response modifier 422 through the epidermis 432 of the body. Tissue response modifier 422 is effective for directing a localized biological response of the body to the implant.

Implant 410 may be any device or material suitable for insertion within a mammalian body. It is desirable that implant 410 be small enough so that tissue displacement and acute inflammation resulting from its implantation is minimized. Implant 410 may be designed to be left in the body after its operational life is over and may include a feature or features designed to maintain location and directionality of the implant. Implant 410 is shown in FIG. 4 disposed in the dermis 434, but one of ordinary skill in the art will appreciate that alternative locations within the body are possible, (e.g., the implant may be disposed in one or more of the hypodermis, the subcutis, the subcutaneous adipose fat, the dermis, an intradermal location, and a subdermal location.)

Implant 410 may be, for example, a sensor (e.g., analyte, electrical, mechanical, and/or thermal sensor), a drug delivery device, a pump, a chip, and combinations thereof.

In the present illustrative embodiment, implant 410 is a glucose sensor comprising a glucose-binding substance. The sensing material is suspended in, contained within, attached to, or otherwise mixed with a hydrogel containing anti-inflammatory drugs or other tissue response modifying drugs. An appropriate amount of this mixture is implanted in the body by hypodermic needle or by microneedle patches that deliver the mixture into the dermis. During the healing process (e.g., over the next 3-7 days), the biosorbable hydrogel dissolves and is absorbed by the body, leaving the sensing material in place in the dermis or subcutis.

Nonsurgical delivery means 420 for delivering a tissue response modifier through the epidermis of the mammalian body may be, for example a cream, a gel, an ointment, a sprayer, a patch, a bandage insert, an array of microneedles, a syringe, combinations thereof, and the like. The nonsurgical delivery means may also comprise one or more of a radiation source (e.g., a source of light, electricity, magnetism, heat, cooling) and a pressure source (used, for example, for laser-induced pressure delivery).

Figure 5:
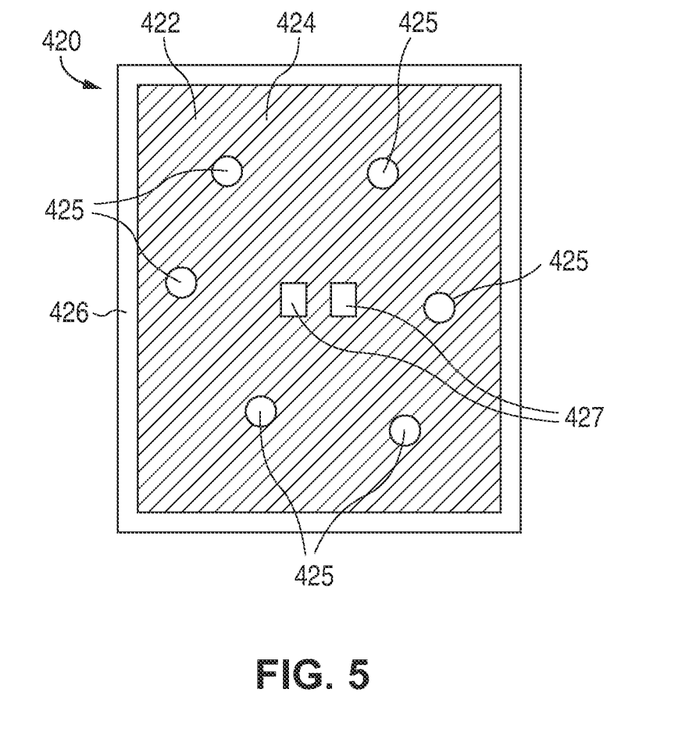
FIG. 5 is a top view of the patch of FIG. 4.

In the present illustrative embodiment, the nonsurgical delivery means is a patch 420, illustrated in side view in FIG. 4 and in top view in FIG. 5. Like reference numbers are used in the drawings to refer to like elements. Patch 420 includes tissue response modifier 422 disposed in a treatment portion 424 of the patch. Patch 420 also includes a backing portion 426 that provides support for treatment portion 424.

Tissue response modifier 422 may be a single modifier or a combination of modifiers. Tissue response modifier 422 may comprise, for example, a collagen inhibitor, an anti-fibrotic agent, an angiogenic agent, a vasculogenic agent, a pro-vascular dilation agent, an immunosuppressive agent, an anti-proliferative agent, an anti-migratory agent, an anti-inflammatory agent, a vasodilator, an anti-histamine, an anti-protein-fouling agent, a metabolic depressor, a synthetic molecule, a biologically produced molecule, a permeation enhancer, a gene therapy agent, a stem cell, a mammalian cell, a drug, and combinations thereof. The tissue response modifier may also comprise light, heat, an electrical pulse, a magnetic field, a magnetic pulse, and combinations thereof.

Specific examples of tissue response modifiers include aspirin, imatinib, celecoxib, rofecoxib, etoricoxib, transforming growth factor β3, interleukin 10, mannose-6-phosphate, cortisone, prednisone, dexamethasone, ibuprofen, cromolyn sodium, halofuginone hydrobromide, tranilast, perfenidone, D-penicillamine, 1-butyryl-glycerol, adenosine, methrotrexate, mycophenolate mofetil, tacrolimus, paclitaxel, rapamycin, doxorubicin, azathioprene, losartan potassium, mitomycin C, diclofenac, dexamethasone, ketoprofane, prostscylin, nifedipine, loratadine, nedocromil, detergents, tissue necrosis factors and/or their inhibitors, platelet derived growth factor, portions of these molecules, sense or anti-sense molecules, and combinations thereof. The above lists are not intended to be exhaustive; additional, unnamed tissue response modifiers are anticipated to be effective in the system.

The delivery means may also include a material effective to target delivery of the agent to a specific location within the body or to modulate uptake of the therapeutic agent by the body. The delivery means may further comprise a component that is related to or interacts with the implant. For example, the delivery means may include an illuminator, a detector, a signal receiver, a signal transmitter, an energy storage component, a data storage component, and combinations thereof.

In the present embodiment, patch 420 as illustrated includes six illuminators 425 and two detectors 427, which together make up an interrogator that is capable of transmitting an interrogating signal to sensor 410 and receiving a sensor signal response. One skilled in the art will appreciate that the precise number of illuminators and detectors is not material to the practice of the invention.

Where interrogation of sensor 410 is optical, for example, illuminators 425 may comprise an LED (light emitting diode) or laser diode or other light source, and detectors 427 may comprise filtered p/n diodes that detect the transmitted or reflected light (absorbance spectroscopy) or emissions (fluorescence). The LED may be a filtered micro-LED in the NIR (near-infrared) region. Such LEDs efficiently illuminate through the skin. In the illustrative glucose sensor described above, the glucose-binding chemistry fluoresces at a different wavelength or absorbs a specific NIR region proportional to the amount of glucose bound to the sensing media. The fluorescent light or absorbed NIR light transmits back through the skin and is detected by the filtered p/n diodes arrayed in the patch.

In another embodiment, the interrogator may comprise a voltage source (as the illuminator) for providing a source signal; an antenna operable with the sensor for transmitting a source signal to the sensor and receiving a signal therefrom; first and second frequency filters (as the detector) operable with the voltage source for receiving the source signal therefrom and providing first and second reference signals; first and second multipliers receiving the interrogation signal and the first and second reference signals, respectively, for providing first and second product signals therefrom; and first and second integrators for receiving the first and second product signals and providing signals indicative of pressure at the sensor. The interrogator may further comprise third and fourth multipliers that receive a delayed interrogation signal and the first and second reference signals and provide third and fourth product signals therefrom, and third and fourth integrators for receiving the third and fourth product signals, respectively, and providing signals indicative of temperature at the sensor.

In the present embodiment, illustrated in FIGS. 4 and 5, illuminators 425 and detectors 427 are integral elements of patch 420. In another embodiment, one portion of the interrogator may be included in the delivery means, while the other portion is implanted separately from but adjacent to the sensor. For example, the detector may be associated with the patch, and the illuminator portion may be implanted adjacent to the sensor; however, the positions may be reversed, with the detector adjacent to the sensor and the illuminator associated with the patch. Alternatively, neither the illuminator nor the detector may be associated with the patch. The invention admits variation in the configuration of the components.

A controller, not shown, may also be associated with patch 420. The controller receives signals from the interrogator, performs signal analysis, and calculates the analyte concentration.

Patch 420 may include an array of microneedles or tissue response modifier-eluting channels. Alternatively, patch 420 may comprise a transdermal delivery preparation such as a cream, a gel, or an ointment that includes tissue response modifier 422. As noted above, microneedles and transdermal delivery preparations may also serve as stand-alone delivery means.

Patch 420 is intended to be disposable. It includes sufficient tissue response modifier to last for a specified application period. Once the tissue response modifier is depleted, the user is alerted via instructions or an included signal to change the patch. It is anticipated that multiple patches will be required to achieve long-term use of the implant.

EXAMPLES

The following examples serve to illustrate, but not to limit, the present invention.

Example 1

Skin Preparation
Sensing Media Insertion
Post-Healing Patch
Sensor Maintenance Patch Assembly
Explant Patch A 0.75 cm×2 cm rectangular skin preparation patch containing 300-750 µg of betamethasone, 3.5 mg/gm neomycin base, 10,000 polymyxin B units/gm, and 0.5% hydrocortisone acetate 5 mg (0.5%) is placed on the skin over the site of implantation, where it adheres to the skin by an adhesive covering the bottom surface of the patch. The drugs are contained in a section of the adhesive, and drug diffuses during the next 12-24 hours through the skin. The skin preparation patch also has a 1- to 2-mm hole near one edge that is used to guide the implantation process. The analyte sensing media, such as a 0.5 mm×10 mm rod-shaped pHEMA hydrogel implant containing analyte sensing chemicals, such as concanavalin A and dextran, or a phenylboronic-derivatized hydrogel backbone, or other reversible ligand-binding analyte pair, is inserted by syringe using the guide hole into the dermis or subcutis 0.5-5.0 mm below the surface. The skin preparation patch is removed, and the skin is cleansed. A 1.5- to 3-cm circular topical drug post-insertion healing patch containing 25 mg of 1% wt/vol of sildenafil or other nitric oxide synthase inhibitor, 10 mg of 2.5%-25% of L-arginine, and/or 2.5 mg of estradiol, is placed on the skin over the site of implantation, where it adheres to the skin by an adhesive covering the bottom surface of the patch. These drugs or agents may be contained in the entire surface adhesive, in a section of the adhesive, or in a mechanical depot within the patch with manifold orifices over the prescribed surface above the implant, and the drugs diffuse through the skin to achieve an effective local concentration to encourage controlled neovascularization, vascular permeability, and control of overactivity of macrophages during implant tissue ingrowth and healing. The patch remains in place for 24-48 hours, and is then removed. A sensor maintenance patch assembly, comprising a drug delivery interface and an electronic signal interrogation component (e.g., light-emitting diodes and filtered photodiodes for fluorescence), is placed over the site of the implant. The drug delivery component provides, for example, an adhesive for adhering the patch to the skin. The drug delivery component contains 125 mg of 65- to 100-mM mannose-6-phosphate or 5% wt/wt halofuginone, and 100 mg of 2.5%-25% L-arginine, to inhibit collagen capsule formation and to maintain adequate blood vessel dilation, respectively. This patch is left on the skin for 5-15 days, and during this time the interrogator collects data from the implant. After 5-15 days, the patch is removed and the two components are separated. The drug delivery component is discarded, and a new drug delivery component is assembled to the electronic signal interrogation component, and the assembly is then placed over the implant site. Analyte sensing media interrogation then resumes. These steps may be repeated as long as necessary. At the end of the operational life of the implanted analyte sensing media, an explantation preparation patch containing 50-150 mg of 0.1% dexamethasone is placed over the analyte sensing media implant site and allowed to stay in place for 3 days. The patch is then removed, and the analyte sensing media is safely explanted.

Example 2

Skin Preparation
Sensing Media Insertion
Sensor Maintenance Patch

A skin preparation patch is placed on the skin at the future implant site 6-24 hours before implantation of an implantable analyte sensor (e.g., glucose, lactate, pruvate, glycerol, urea). The skin preparatory patch contains 50-150 mg of 0.1% dexamethasone, which is released at a rate sufficient to achieve localized concentrations of 0.05-20.0 mg/kg in an area ranging from 0.5 cm to 4.0 cm in diameter and 0.05 cm to 1.0 cm in depth. The patch also contains a temporary skin colorant, e.g., 2-hydroxy-1,4-naphthoquinone (also called Henna), which will diffuse into the skin to demarcate the area that has been directly exposed to the dexamethasone. Alternatively, a wide selection of temporary transfer tattoo inks may be utilized as the temporary colorant in the skin preparatory patch. Yet another alternative for use as the temporary skin colorant is providone iodine (Betadine®), which can also sterilize the skin in preparation for injection, incision or other planned perforations of the skin barrier. Yet another alternative skin colorant to denote the implant area is a substance that will be visible only under UV light, such as sodium fluorescein, which is widely used and considered safe for epi-cutaneous labeling. After 2-24 hours, the skin preparation patch is removed, and the analyte sensor is implanted. Alternatively, implantation may take place prior to removing the pre-implant patch, thus avoiding the need for colorant, or the individual applying the patch may mark the skin with a marking pen or other implement before placing the patch.

The analyte sensing media is implanted via a syringe-like injection system at a depth under the outer surface of the skin ranging from 0.05 to 1.0 cm. The skin colorant, which was delivered by the skin preparatory patch and which remains visible on the skin under normal or UV light, is used as a visual guide to placement of the implant. The area of sensing media implantation coincides with the colorant demarcating the area of the skin that received the dexamethasone, which was delivered from the skin preparation patch.

Immediately after sensing media insertion, a second patch, called a post-insertion healing patch, is applied above the implant that delivers 0.01-3% diclofenac sodium, 3.5 mg/gm neomycin base, 10,000 polymyxin B units/gm, and 0.5% hydrocortisone acetate 5 mg (0.5%). The post-insertion healing patch releases contents in an area ranging from 0.5 cm to 4.0 cm in diameter and to a depth ranging from 0.05 cm to 1.0 cm. The post-insertion healing patch is left in place for 3 to 7 days, after which time it is removed.

After the removal of the post-insertion healing patch, the surface of the skin in the area of the analyte sensing media is washed with mild detergent to remove surface oils and rinsed thoroughly with water. The area is swabbed with rubbing alcohol and allowed to air-dry. A third patch type, the sensor maintenance patch, is then applied to the surface of the skin over the analyte sensing media site. The sensor maintenance patch contains 5% wt/wt halofuginone or 125 mg of 65- to 100-mM mannose-6-phosphate to inhibit collagen synthesis and prevent collagen capsule formation within or around the analyte sensing media. The sensor maintenance patch also contains electronics for optical interrogation of the sensor and radio frequency communication. Upon placement of the sensor maintenance patch, the patient conducts a 2 point capillary blood glucose calibration, and begins taking readings. Every 7 days, a patch replacement procedure is conducted. The old sensor maintenance patch is removed; the area is washed with a mild detergent, rinsed thoroughly with water, dried, swabbed with rubbing alcohol, and allowed to air-dry. A fresh replacement sensor maintenance patch is then applied over the implant, and a capillary blood glucose calibration is conducted. Collection of analyte measurements then resumes. The sensor maintenance patch replacement procedure is conducted every 7 days throughout the lifetime of the inserted sensor.

After the useful life of the analyte sensing media, the sensor maintenance patch is removed, and the area is washed, rinsed, and swabbed with disinfectant. The analyte sensing media is then removed via a minimal incision. To continue analyte measurements, a fresh analyte sensing media may be implanted in a different location following the above procedure (including application of a skin preparation patch). The new analyte sensing media may be implanted greater than 2 cm away from the first sensor. This entire procedure may be repeated as many times as needed to replace a sensor whose useful life has expired. Also, this entire procedure may be repeated as many times as needed for insertion of multiple analyte sensors.

Example 3

Analyte Sensing Media Insertion
Post-Implant Healing Patch
Sensor Maintenance Patch Analyte sensing media, such as a 0.5 mm×10 mm rod-shaped pHEMA hydrogel implant containing analyte sensing chemicals, such as concanavalin A and dextran, or a phenylboronic-derivatized hydrogel backbone, or other reversible ligand-binding analyte pair, is implanted into the dermis 0.5 mm to 5 mm below the surface of the skin by syringe or catheter. A 1.5- to 3-cm circular topical drug post-insertion healing patch containing 25 mg of 1% wt/vol of sildenafil or other nitric oxide synthase inhibitor, 10 mg of 2.5%-25% of L-arginine, and/or 2.5 mg of estradiol, is placed on the skin over the site of implantation, where it adheres to the skin by an adhesive covering the bottom surface of the patch. These drugs or agents may be contained in the entire surface adhesive, in a section of the adhesive, or in a mechanical depot within the patch with manifold orifices over the prescribed surface above the implant, and the drugs diffuse through the skin to achieve an effective local concentration to encourage controlled neovascularization, vascular permeability, and control of overactivity of macrophages during implant tissue ingrowth and healing. The patch remains in place for 24-48 hours, and is then removed.

After this period, a sensor maintenance patch comprising a drug delivery interface (e.g., cream, ointment, microneedles, iontophoretic electrode and drug reservoir) and an electronic signal interrogation interface (e.g., light-emitting diodes and filtered photodiodes for fluorescence) is placed over the site of the implant. The drug delivery component contains 100 mg of L-arginine, and 125 mg of 65- to 100-mM mannose-6-phosphate or 100 mg of 5% wt/wt halofuginone. The L-arginine maintains blood flow through the newly generated microvessels within the implant, and low-dose mannose-6-phosphate or halofuginone inhibit overabundant Type 1 collagen capsule formation, which would otherwise reduce diffusion of analyte to the sensor. This patch is left on the skin for 3-14 days, and during this time the interrogator collects data from the implant. After 3-15 days, the sensor maintenance patch is removed and discarded, and another sensor maintenance patch is placed over the implant site, and interrogation of the sensor implant continues. These latter steps may be repeated as long as necessary.

Example 4

Analyte Sensing Media Insertion
Post-Implant Healing
Interrogation Only
Explant Patch A 0.5 mm×10 mm rod-shaped hydrogel implant containing analyte sensing chemicals, such as concanavalin A and dextran, or phenylboronic derivatized hydrogel backbone, or other reversible ligand-binding analyte pair, is implanted into the dermis 2-3 mm below the surface by syringe or catheter. A post-insertion healing patch is applied above the implant that delivers 25 mg of 17B estradiol, 0.01-3% diclofenac sodium, an NSAID (non-steroidal anti-inflammatory drug), 3.5 mg/gm neomycin base, 10,000 polymyxin B units/gm, and 0.5% hydrocortisone acetate 5 mg (0.5%). The post-implant healing patch releases contents in an area ranging from 0.5 cm to 4.0 cm in diameter and a depth ranging from 0.05 cm to 1.0 cm. The post-implant healing patch is left in place for 3 to 7 days, after which time it is removed. After the removal of the post-insertion healing patch, the surface of the skin in the area of the implant is washed with mild detergent to remove surface oils and rinsed thoroughly with water.

After this healing period, an interrogation patch—comprising light-emitting diodes and filtered detector photodiodes, microprocessor, power source, and RF communication module, for fluorescence detection—is placed on the skin over the implant site and allowed to stay in place for 30-180 days. The interrogation patch may be held in place by an adhesive that is replenished every 5-15 days or by a strap or other means to hold the patch against the surface of the skin. During this time, data are continuously collected from the implant.

If an adhesive is used, after a period of 5-15 days, the interrogation patch is removed and the adhesive component is replaced with a fresh adhesive component, and the interrogation patch is placed back on the skin over the implant. This procedure may be repeated as often as necessary over the life of the implant.

When the implant reaches the end of its operational life, a cream or ointment containing 0.05% clobetasol 17-propionate is applied to the skin above the implant 2-3 times per day for 24-72 hours to prepare the tissue for explantation. This encourages devascularization of the implant. The implant is then removed.

Example 5

Skin Preparation
Analyte Sensing Media Insertion
Interrogation
Explant Patch

A skin preparation cream or ointment containing a mild to moderately potent steroid, e.g., 0.25% fluocinolone acetonide or 1% hydrocortisone acetate, is applied to a 1- to 4-cm diameter area of skin where an analyte sensing media will later be implanted. Application of the cream or ointment is repeated every 4-6 hours for at least 24 hours. The cream or ointment is removed and the analyte sensing media is placed into the dermis 0.5 mm to 10 mm below the surface of the skin. For the next 7-10 days the implant is allowed to heal in place. After this healing period, an interrogation patch—comprising light-emitting diodes and filtered detector photodiodes, microprocessor, power source, and RF communication module, for fluorescence detection—is placed on the skin over the implant site and allowed to stay in place for 30-180 days. The interrogation patch may be held in place by an adhesive that is replenished every 5-15 days or by a strap or other means to hold the patch against the surface of the skin. During this time, data are continuously collected from the implant. If an adhesive is used, after a period of 5-15 days, the interrogation patch is removed and the adhesive component is replaced with a fresh adhesive component, and the interrogation patch is placed back on the skin over the implant. This procedure may be repeated as often as necessary over the life of the implant.

When the implant reaches the end of its operational life, a cream or ointment containing 0.05% clobetasol 17-propionate is applied to the skin above the implant 2-3 times per day for 24-72 hours to prepare the tissue for explantation. This encourages devascularization of the implant. The implant is then removed.

Example 6

Skin Preparation
Analyte Sensing Media Insertion
Post-Insertion Healing
Sensor Maintenance Patch
Explant Patch A 0.75 cm×2 cm rectangular skin preparation patch containing 300-750 µg of betamethasone is placed on the skin over the site of implantation, where it adheres to the skin by an adhesive covering the bottom surface of the patch. The drug is contained in a section of the adhesive, and drug diffuses during the next 12-24 hours through the skin and achieves a dermal concentration of in the range of 0.1-1.0 µg/mL wt/vol in the tissue below. The formulation may contain a carrier and penetrant additive(s) to facilitate penetration. Betamethasone blocks certain aspects of the acute inflammation response in preparation for the implant to be placed into the tissue. The skin preparation patch also has a 1- to 2-mm hole near one edge that is used to guide the implantation process. The analyte sensing media is then placed via a syringe or catheter through the guide hole into the dermis or subcutis 0.5-5.0 mm below the surface. The skin preparation patch is then removed. A second patch, a post-insertion healing patch, containing 25 mg of 17B estradiol to facilitate healing as well as a small amount of non-steroidal anti-inflammatory compound to dampen other aspects of the acute inflammatory response, is applied over the site of implantation. This skin preparation patch is left in place for 24 hours, and then it is removed. The implant is then allowed to heal in place for the next 7-10 days. During this time, tissue in-growth, neovascularization, and tissue modification occurs.

After the healing phase, a sensor maintenance patch, comprising a drug delivery interface (e.g., cream, ointment, microneedles, iontophoretic electrode and drug reservoir) and an electronic signal interrogation component (e.g., light-emitting diodes and filtered photodiodes for fluorescence), is placed over the site of the implant. The drug delivery component provides an adhesive for adhering the patch to the skin. The drug delivery component contains 125 mg of 65- to 100-mM mannose-6-phosphate or 5% wt/wt halofuginone, and 100 mg of 2.5%-25% L-arginine, to inhibit collagen capsule formation and to maintain adequate blood vessel dilation, respectively. This patch is left on the skin for 5-15 days, and during this time the interrogator collects data from the implant.

After 5-15 days, the patch is removed and the two components are separated. The drug delivery component is discarded, and a new drug delivery component is assembled to the electronic signal interrogation component, and the assembly is then placed over the implant site. Analyte sensing media interrogation then resumes. These steps may be repeated as long as necessary.

At the end of the operational life of the implanted analyte sensing media, an explantation preparation patch containing 50-150 mg of 0.1% dexamethasone is placed over the analyte sensing media implant site and allowed to stay in place for 3 days. The patch is then removed and the analyte sensing media is safely explanted.

Example 7

Skin Preparation
Insertion
Light Treatment
Interrogation/Maintenance
Explant Patch A skin preparation cream or ointment containing 0.05% betamethasone or 1% hydrocortisone acetate is applied to a 1- to 4-cm diameter area of skin where an analyte sensor will later be implanted. The application is repeated every 6 hours for 24-48 hours. Then the analyte sensing media, such as described in other examples above, is then implanted into the dermis 0.5-5 mm below the surface by syringe or catheter. An adhesive band containing light emitting diodes or lasers to provide localized phototherapy is then applied to the skin after implantation over the area of implantation. The patch containing a cluster of 6 to 48 LED photons at 510-543, 594-599, 626-639, 640-670 842-872, and 1049-1082 nm wavelengths with 50-500 mW output power, is placed over the implantation area. 2-15 J/cm$^2$ treatments are administered 1-3 times daily to reduce inflammation and reduce damaging reactive oxygen species in the wound healing environment. Alternatively, a non-coherent light at 890 nm may be applied, which directs macrophages to send inhibitory signals to quiet fibroblast activity. Alternatively, or additionally, a light source at 625-635 nm may be used that inhibits cyclooxygenase (COX) and prostaglandin E(2) (PGE(2)), to reduce reactive oxidative species, and promote diabetic wound healing. Inhibition of COX and (PGE(2)) protects cells against cell injury in specific pathophysiological situations: inflammation and oxidative stress. Alternatively or additionally, a light source at 1072 nm light may be used, which has been shown to upregulate production of cytoprotective species (e.g., indicible nitric oxide synthase). Specified phototherapy depends on the stage of wound healing and foreign body response (e.g., initially anti-inflammatory 625-635 nm light may be used, and later, as the foreign body reaction ensues, 890 nm light to calm fibroblast activity and 1072 nm light to enhance NO production may be utilized). This treatment facilitates healing of the implant in the implant site and proceeds for 48-72 hours.

After treatment, a sensor maintenance patch containing 5% wt/wt halofuginone or 125 mg of 65- to 100-mM mannose-6-phosphate is placed to inhibit collagen synthesis and prevent collagen capsule formation within or around the analyte sensing media. The sensor maintenance patch also contains electronics for optical interrogation of the sensor and radio frequency communication. After this period, a second patch, comprising a drug delivery interface (e.g., cream, ointment, microneedles, iontophoretic electrode and drug reservoir) and an electronic signal interrogation interface (e.g., light-emitting diodes and filtered photodiodes for fluorescence), is placed over the site of the implant. The drug delivery component contains 100 mg of L-arginine, and 125 mg of 65- to 100-mM mannose-6-phosphate or halofuginone. The L-arginine maintains blood flow through the newly generated microvessels within the implant, and low-dose mannose-6-phosphate or halofuginone inhibit overabundant collagen capsule formation for optimal analyte diffusion. This patch is left on the skin for 3-14 days, and during this time the interrogator collects data from the implant.

After 5-15 days, the patch is removed and discarded, and another interrogation/drug patch is placed over the implant site, and interrogation of the sensor implant continues. These latter steps may be repeated as long as necessary.

The same patch described above with multiple wavelength LED clusters may be controlled via an external device (cell phone, hand-held, wristwatch, computer or other device) to activate certain LEDs and turn off others in order to change delivery wavelengths and/or intensity of phototherapy.

Example 8

Insertion
Healing Phototherapy
Interrogation Plus Maintenance Therapy

An electrochemical glucose sensor is implanted subcutaneously. For 1-3 weeks following implantation, tissue response modifiers in the form of specific wavelengths and intensity of light are delivered 1-3 times daily for 0.5-3.0 minutes from a portable hand-held device. This device is similar to a miniaturized version of the Biolux Research light emitting diode phototherapy device. Treatment is administered by the patient, who holds the light emitting portion of the device against the skin in the area of the implant for 0.5-3.0 minutes a day at an energy density of 1-50 mW/cm$^2$. The total dosage to the surface of the skin overlying the implant is 6-20 J/cm². This phototherapy regimen accelerates healing and improves angiogenesis. Optionally, silver oxide cream is applied twice daily to the implant area to enhance wound healing. After 1-3 weeks of localized phototherapy and application of silver oxide cream, the sensor has sufficiently healed into the tissue, and analyte measurements are ready to be taken. A hand-held RFID (radio frequency identification) and wireless battery charging device is placed in contact with the skin over the implant (may be the same device from which phototherapy was delivered above). The implant sends a signal to the hand-held and its internal battery is recharged wirelessly.

Upon initial use and once a week thereafter, a calibration procedure is performed that requires patients to measure capillary blood glucose using traditional fingerprick methods and enter that data into the hand-held device. The hand-held then converts the sensor signal to a glucose reading that is displayed to the patient. Any time the patient wishes to take a glucose reading, the hand-held device is held next to the skin.

Maintenance phototherapy may be delivered to the implant area 1-7 times a week for 0.5-10 minutes to insure the integrity of the tissue-sensor interface is maintained in a condition appropriate to generate sensor signals that reflect blood glucose readings. If continuous glucose monitoring is required rather than frequent checks that can be performed with the hand held (e.g., at night time for insulin dependent children), the patient may attached an RFID patch to the implant area, which will wirelessly transmit the signal coming from the electrochemical sensor to the hand-held device.

Example 9

Implant Drug Pump
Healing Patch

A fully implantable drug pump is implanted subcutaneously. Optionally, NSAID and utercalin microspheres are implanted adjacent to the pump outlet. A post-implantation healing patch, containing 25 mg of 17B estradiol, 0.01-3% diclofenac sodium, an NSAID, 3.5 mg/gm neomycin base, 10,000 polymyxin B units/gm, and 0.5% hydrocortisone acetate 5 mg (0.5%), is applied. This patch is left in place for 24 hours, and then it is removed. The patch-delivered drugs and the implanted microsphere-delivered drugs heal and condition the tissue around the pump outlet to prevent foreign body response occlusion of the outlet. The condition of the tissue around the pump outlet is maintained by replacing the patch with a maintenance patch containing 125 mg of 65- to 100-mM mannose-6-phosphate or 5% wt/wt halofuginone, and 100 mg of 2.5%-25% L-arginine. The maintenance patch may be replaced periodically.

It should be noted that all implanted devices undergo a host response by the individual receiving the implant. Thus, the presently described methods and systems may be used with other bio- or chemisensors, micromechanical sensing devices, thermal sensing devices, in vitro network microappliances, and prosthetic implants.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A system comprising:
an implant configured to be placed within a mammalian body, the implant configured to sense an analyte within the mammalian body, the implant having a first sensitivity to the analyte before a foreign body response of the mammalian body and a second sensitivity less than the first sensitivity after the foreign body response of the mammalian body;
a first patch configured to be placed on a surface of the mammalian body and to deliver a first tissue response modifier such that the first tissue response modifier does not reach systemic levels in the mammalian body, the first tissue response modifier configured to, at least one of, (1) minimize a first response of the mammalian body to the implantation of the implant or (2) enhance a second response of the mammalian body to the implantation of the implant; and
a second patch configured to be placed on the surface of the mammalian body over the implant after the first patch is placed on the surface of the surface of the mammalian body, the second patch configured to (1) receive a signal from the implant associated with the analyte, and (2) deliver a second tissue response modifier through an epidermis of the mammalian body to reduce or eliminate the foreign body response of the mammalian body, the second patch configured to deliver the tissue response modifier such that the tissue response modifier does not reach systemic levels in the mammalian body.

2. The system of claim 1, further comprising:
a third patch configured to be placed on the mammalian body after the first patch, the third patch configured to (1) receive the signal from the implant and (2) deliver a third tissue response modifier through an epidermis of the mammalian body such that the third tissue response modifier does not reach systemic levels in the mammalian body.

3. The system of claim 1, wherein the second patch is configured to be placed on surface of the mammalian body before the implant is placed within the mammalian body.

4. The system of claim 1, wherein the implant includes a hydrogel surrounding a sensing material, the hydrogel configured to be bioabsorbed by the mammalian body when the implant is placed into the mammalian body exposing the sensing material to a tissue of the mammalian body.

5. The system of claim 1, wherein the patch is configured to be removable from the mammalian body.

6. A method for using the system of claim 1, the method comprising:
positioning the first patch on the surface of the mammalian body;
delivering the first tissue response modifier from the first patch such that the first tissue response modifier does not reach systemic levels in the mammalian body;
positioning the second patch on the surface of the mammalian body over the implant after the first patch is positioned; and
delivering the second tissue response modifier from the second patch through the epidermis of the mammalian body to reduce or eliminate the foreign body response of the mammalian body such that the second tissue response modifier does not reach systemic levels in the mammalian body.

7. The method of claim 6 further comprising:
removing the first patch prior to positioning the second patch.

8. The method of claim 6 wherein delivering the first tissue response modifier includes injecting the first tissue response modifier from the first patch into the mammalian body through skin tissue disposed between the first patch and the implant.

9. The method of claim 6 wherein the first patch includes a material effective to modulate uptake of the first tissue response modifier by the body.

10. The method of claim 6 wherein the first patch includes at least one of an illuminator, a detector, a signal receiver, a signal transmitter, an energy storage component, or a data storage component.

11. The method of claim 6 further comprising:
removing the implant from the mammalian body after delivering the second tissue response modifier.

12. A system, comprising:
an implant configured to be placed within a mammalian body, the implant configured to measure an analyte of the mammalian body, the implant having a first sensitivity to the analyte before a foreign body response of the mammalian body and a second sensitivity less than the first sensitivity after the foreign body response of the mammalian body;
a first patch configured to be placed on a surface of the mammalian body over the implant, the first patch configured to (1) receive a signal from the implant associated with the analyte, and (2) deliver a first tissue response modifier through an epidermis of the mammalian body to reduce or eliminate the foreign body response of the mammalian body, the first patch configured to deliver the tissue response modifier such that the tissue response modifier does not reach systemic levels in the mammalian body; and
a second patch configured to be placed on the mammalian body after the first patch, the second patch configured to (1) receive the signal from the implant and (2) deliver a second tissue response modifier through an epidermis of the mammalian body such that the second tissue response modifier does not reach systemic levels in the mammalian body.

13. The system of claim 12, wherein:
the implant includes a sensing material configured to bind to the analyte and produce the signal in proportion to a quantity of the analyte, the foreign body response reducing an availability of the analyte to the sensing material; and
the first patch includes a detector that receives the signal from the sensing material of the implant.

14. The system of claim 13 wherein the first patch further comprises at least one of an illuminator, a signal receiver, a signal transmitter, an energy storage component, or a data storage component.

15. The system of claim 13, wherein the first patch further comprises at least one of a radiation source and a pressure source.

16. The system of claim 13 wherein the first patch further comprises an interrogator configured to transmit an interrogating signal through the epidermis to the sensing material of the implant.

17. The system of claim 13, wherein:
the effectiveness of the sensing material is degraded by a local accumulation of collagen; and
the first tissue response modifier inhibits the local accumulation of collagen.

18. The system of claim 13, wherein the effectiveness of the sensing material is degraded when the analyte is impeded from reaching the sensing material by collagen.

19. The system of claim 13, wherein:
the analyte is glucose;
the sensing material is a glucose-binding substance; and
the effectiveness of the glucose-binding substance is impeded by the foreign body response reducing a local concentration of glucose below a systemic concentration of glucose.

20. The system of claim 12, wherein the first tissue response modifier includes at least one selection from a group consisting of a collagen inhibitor, an anti-fibrotic agent, an angiogenic agent, a vasculogenic agent, a pro-vascular dilation agent, an immunosuppressive agent, an anti-proliferative agent, an anti-migratory agent, an anti-inflammatory agent, a vasodilator, an anti-histamine, an anti-protein-fouling agent, a metabolic depressor, a synthetic molecule, a biologically produced molecule, a permeation enhancer, a gene therapy agent, a stem cell, a mammalian cell, and a drug.

21. The system of claim 12, wherein the implant is configured to be placed within at least one of a dermis or a subcutis of a mammalian body.

22. The system of claim 12, wherein the first patch is configured to be removeably coupled to the mammalian body.

* * * * *